(12) United States Patent
Kyakuno et al.

(10) Patent No.: US 11,946,899 B2
(45) Date of Patent: Apr. 2, 2024

(54) MEASURING DEVICE

(71) Applicant: YOKOGAWA ELECTRIC CORPORATION, Tokyo (JP)

(72) Inventors: Toshihiko Kyakuno, Tokyo (JP); Megumi Goto, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 48 days.

(21) Appl. No.: 17/463,772

(22) Filed: Sep. 1, 2021

(65) Prior Publication Data

US 2022/0065814 A1 Mar. 3, 2022

(30) Foreign Application Priority Data

Sep. 3, 2020 (JP) .................. 2020-148518

(51) Int. Cl.
*G01N 27/416* (2006.01)
*G01N 27/38* (2006.01)

(52) U.S. Cl.
CPC ......... *G01N 27/4168* (2013.01); *G01N 27/38* (2013.01)

(58) Field of Classification Search
CPC .. G01N 27/4168; G01N 27/38; G01N 33/182; G01N 27/49; G01N 27/283; G01N 27/406
See application file for complete search history.

(56) References Cited

U.S. PATENT DOCUMENTS

2019/0331640 A1* 10/2019 Kuwagata .............. G01N 27/30

FOREIGN PATENT DOCUMENTS

| CN | 1867874 A | | 11/2006 |
|---|---|---|---|
| JP | 2001091495 A | * | 4/2001 |
| JP | 2001-349866 A | | 12/2001 |
| JP | 2001349866 A | * | 12/2001 |
| JP | 2004053548 A | * | 2/2004 |
| JP | 2004053549 A | * | 2/2004 |
| JP | 2004191197 A | * | 7/2004 |
| JP | 2008-164408 A | | 7/2008 |
| JP | 2009-168694 A | | 7/2009 |
| JP | 2009168694 A | * | 7/2009 |
| JP | 2009236787 A | * | 10/2009 |
| JP | 2015-117939 A | | 6/2015 |
| JP | 2016-080573 A | | 5/2016 |

(Continued)

OTHER PUBLICATIONS

Mihashi et al., English translation of JP-2016080573-A, 2016 (Year: 2016).*

(Continued)

*Primary Examiner* — Joshua L Allen
*Assistant Examiner* — Shizhi Qian
(74) *Attorney, Agent, or Firm* — Osha Bergman Watanabe & Burton LLP

(57) ABSTRACT

A measuring device includes: a first electrode and a second electrode immersed in sample water stored in a measuring tank; a motor that rotates the first electrode; and a controller that operates, based on measurement results of current flowing through the sample water, in a measuring mode. In the measuring mode, the controller calculates a concentration of a measurement target in the sample water. The motor changes a rotational velocity of the motor.

10 Claims, 3 Drawing Sheets

(56) References Cited

FOREIGN PATENT DOCUMENTS

JP       2016080573 A  *  5/2016
JP       2018124130 A  *  8/2018

OTHER PUBLICATIONS

Akazawa et al., English translation of JP2001349866A, 2001. (Year: 2001).*
Kuwagata et al., English translation of JP2009168694A, 2009 (Year: 2009).*
Chinese Office Action with translation dated Jan. 10, 2024, issued for Chinese Patent Application No. 202111030942.0 (13 pages).

* cited by examiner

MEASURING DEVICE

BACKGROUND

Technical Field

The present disclosure relates to a measuring device.

Related Art

The conventional measuring devices measure a chlorine concentration in sample water using an electrode that rotates in the sample water is known (for example, see patent literature 1).

PATENT LITERATURE

Patent Literature 1: JP 2008-164408 A

In the conventional measuring devices, there is room for improvement in convenience.

SUMMARY

One or more embodiments provide a measuring device capable of improving convenience.

A measuring device according to one or more embodiments includes a first electrode and a second electrode immersed in sample water stored in a measuring tank, a motor for rotating the first electrode, and a control unit configured to operate in a measuring mode for calculating a concentration of a measurement target in the sample water based on measurement results of current flowing through the sample water. The motor is configured to be able to change its rotational velocity. Thus, the measuring device can operate in various operation modes. As a result, the convenience of the measuring device is improved.

In the measuring device according to one or more embodiments, the motor may rotate either clockwise or counterclockwise as a forward direction when the rotational velocity is a positive value and rotate in a direction opposite to the forward direction when the rotational velocity is a negative value. The control unit may control the rotation of the motor so as to alternately change the rotational velocity between a positive value and a negative value. Thus, the first electrode is less readily stretched in one direction. As a result, the life of the first electrode is extended.

In the measuring device according to one or more embodiments, the control unit may control the rotation of the motor so as to alternately change the rotational velocity between a positive value and a negative value when operating in the measuring mode or when operating in at least one mode of a cleaning mode for cleaning the first electrode. Thus, the first electrode can be easily cleaned. As a result, the convenience of the measuring device is improved.

In the measuring device according to one or more embodiments, the control unit may control the rotation of the motor such that the absolute value of the rotational velocity when operating in a standby mode where the concentration of a measurement target in the sample water is not calculated is made smaller than the absolute value of the rotational velocity when operating in the measuring mode. Thus, a slip ring electrically connected to the first electrode or the rotating first electrode is less readily abraded. As a result, the life of parts is extended.

In the measuring device according to one or more embodiments, the control unit may stop the motor when operating in the standby mode. Thus, a slip ring electrically connected to the first electrode or the rotating first electrode is less readily abraded. As a result, the life of parts is extended.

The measuring device may further include granular members located inside the measuring tank so as to contact a surface of the first electrode. In the measuring device, the control unit may control the rotation of the motor such that the absolute value of the rotational velocity when operating in a breaking in mode after the granular members are replaced is made larger than the absolute value of the rotational velocity when operating in the measuring mode. Thus, the amount of time until stabilization after replacement of the granular members is shortened. As a result, the convenience of the measuring device is improved.

In the measuring device according to one or more embodiments, the control unit may control the rotational velocity based on the magnitude of a current flowing in a standard sample water having a known measurement target concentration. Thus, the error of the calculation result of the concentration of the measurement target is reduced. As a result, the convenience of the measuring device is improved.

According to one or more embodiments, a measuring device capable of improving convenience is provided.

DETAILED DESCRIPTION

Figure 1:
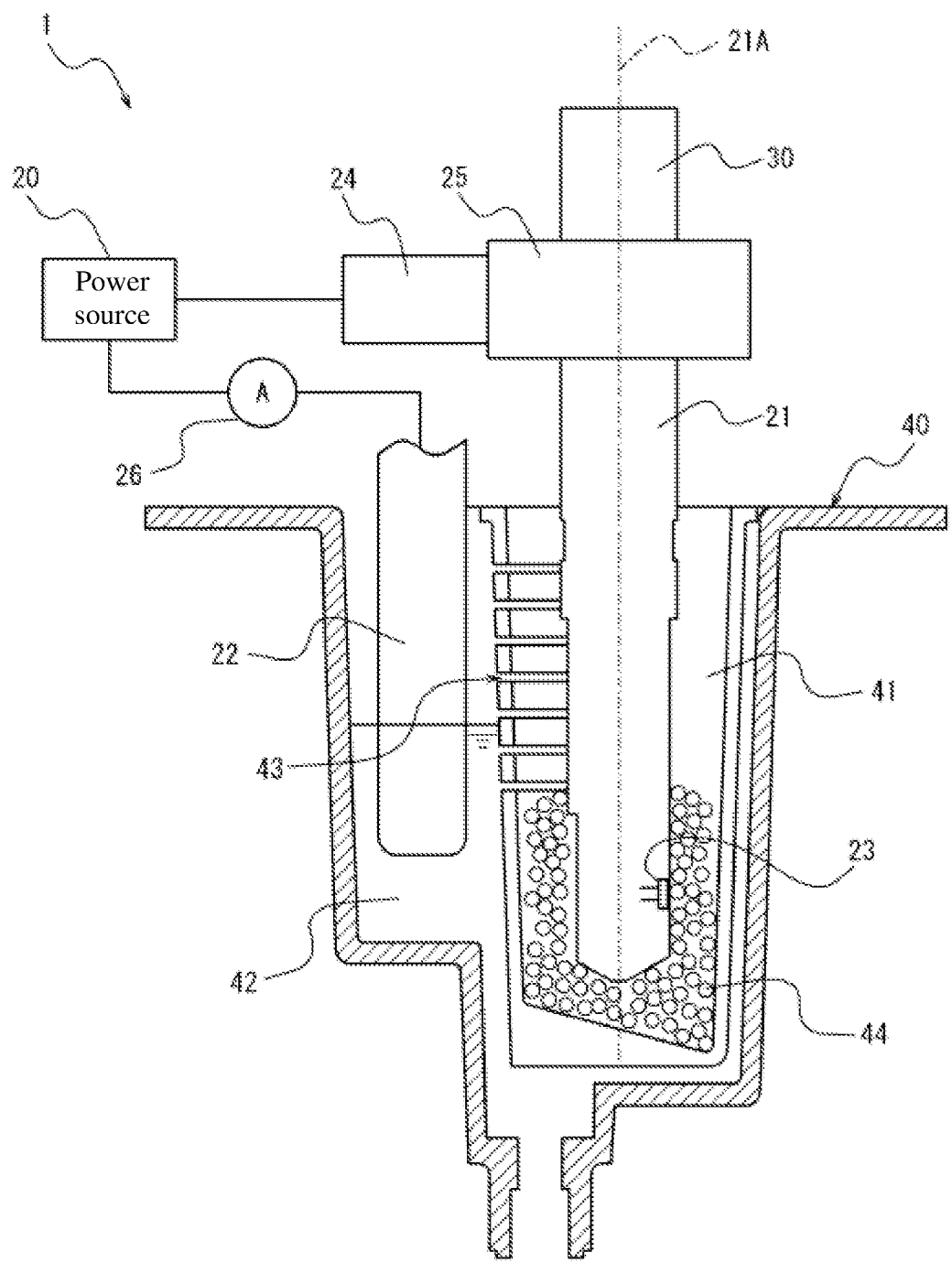
FIG. 1 is a sectional view illustrating a configuration example of a measuring device according to one or more embodiments.

Embodiments of the present invention will be described herein with reference to the drawings. According to one or more embodiments, a measuring device 1 (see FIG. 1) measures a concentration of a measurement target in sample water. The measuring device 1 applies a predetermined voltage to sample water in which an electrode is immersed, measures a current flowing through the water, and calculates a concentration of a measurement target in the sample water based on the measured value of the current. The measurement target may include, for example, chlorine, bromine, or iodine. The measurement target may include, for example, a metal ion.

The measuring device 1 measures a diffusion current flowing between two electrodes immersed in the sample water. The measuring device 1 rotates the electrodes to stabilize a diffusion layer contributing to the magnitude of the diffusion current.

The magnitude of the diffusion current is affected by the states of the electrodes. For example, dirtiness of the surface of the electrode changes the magnitude of the diffusion current. In order to stabilize the state of the electrode contributing to the magnitude of the diffusion current, the measuring device 1 cleans the surface of the electrode by bringing granular members 44 (see FIG. 1 and the like) such as ceramic beads or glass beads into contact with the surface of the electrode. The surface of the electrode is cleaned by the granular members 44 and may be deformed or abraded by friction with the granular members 44. Deformation or abrasion of the surface of the electrode shortens the life of the electrode.

The measuring device 1 includes a configuration for bringing a brush 24 (see FIG. 1 and the like) into contact with a rotating slip ring 25 (see FIG. 1 and the like) in order to make the rotating electrode electrically continuous with another circuit. The slip ring 25 and the brush 24 realize a rotary sliding function. The slip ring 25 or the brush 24 is abraded by friction. The life of the slip ring 25 or the brush 24 is shortened by abrasion.

The greater the deformation or abrasion of the electrode or the abrasion of the slip ring 25 or the brush 24, the shorter the life of each part is. It is sought to prolong the life of each part.

The measuring device 1 according to one or more embodiments will be described below while being compared against a comparative example.

A measuring device of a comparative example for the measuring device 1 according to the present disclosure is described. The measuring device according to a comparative example includes a driving device for rotating an electrode at a constant velocity in one direction. Specifically, in a period when the measuring device is in a started state, the driving device is always energized and rotates at a constant velocity in one direction. Here, in the period while in the started state, the measuring device measures the current at a time determined by a predetermined sampling period and does not measure the current at any other times. That is, the measuring device according to the comparison example rotates the electrode at a constant velocity in one direction at all times regardless of whether current is measured during the period while in the started state. In which case, the deformation or abrasion of the electrode or the abrasion of the slip ring 25 or the brush 24 continues to occur during the period while in the started state. As a result, the life of the parts of the measuring device is shortened.

According to one or more embodiments, the measuring device 1 is capable of prolonging the life of parts.

Figure 2:
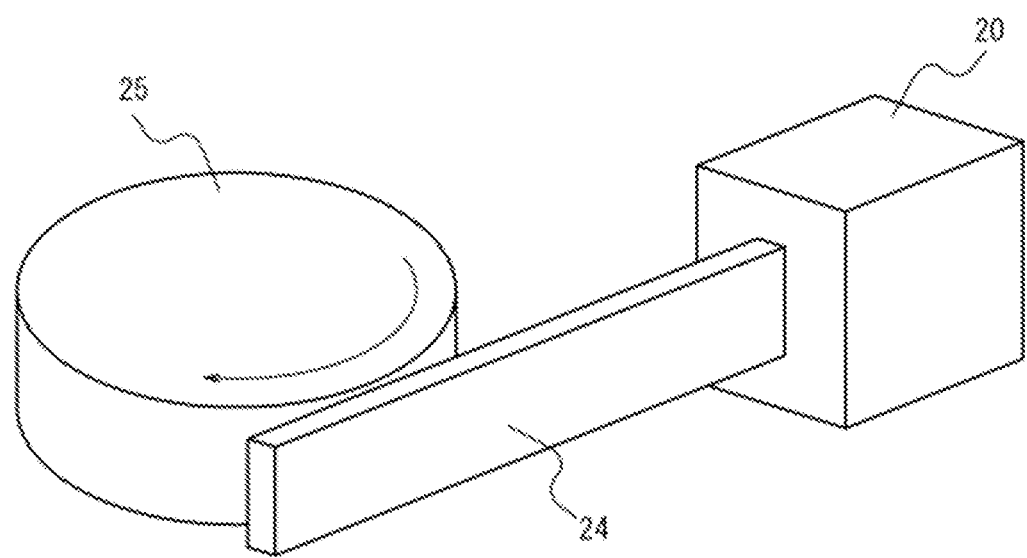
FIG. 2 is a drawing illustrating a configuration example of a slip ring.
Figure 3:
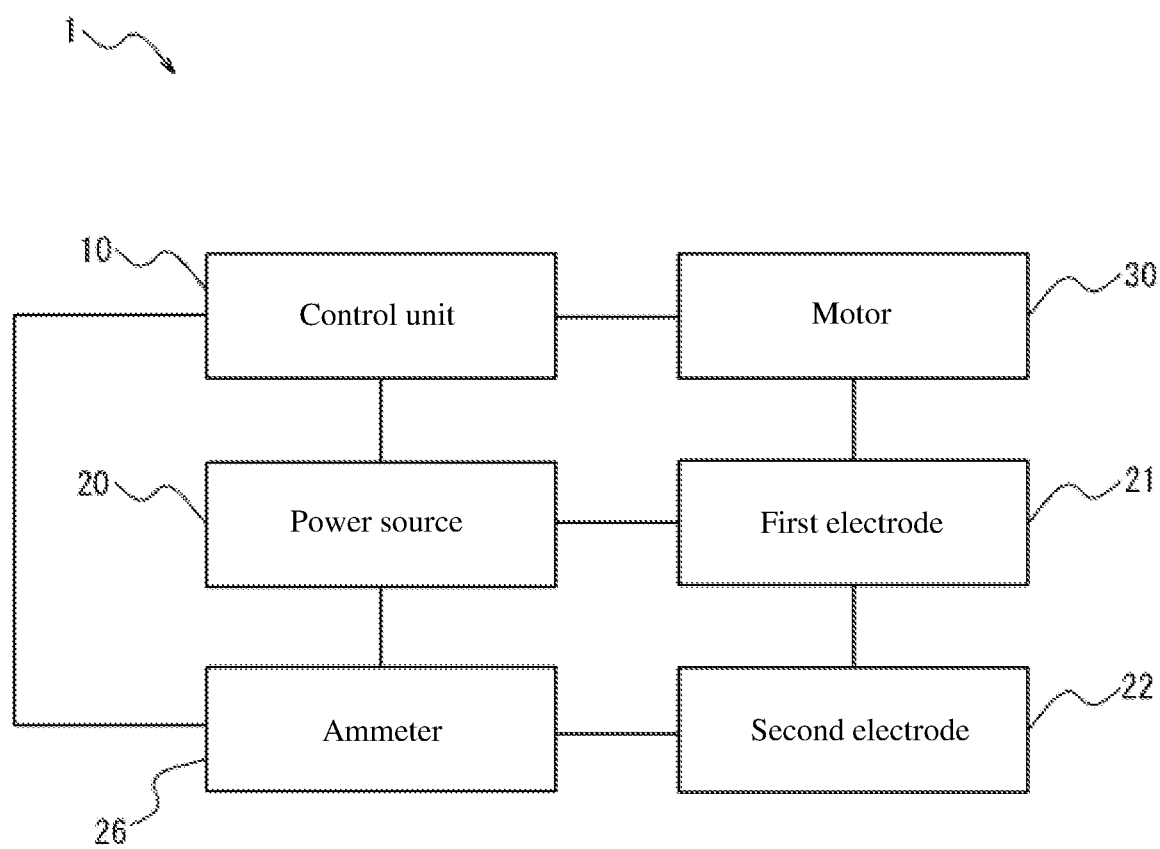
FIG. 3 is a block diagram illustrating a configuration example of a measuring device according to one or more embodiments.

As illustrated in FIGS. 1-3, a measuring device 1 according to one or more embodiments includes a measuring tank 40, which stores sample water, and a measuring unit that measures a characteristic of the sample water by flowing a current through the sample water. In one or more embodiments, the measuring device 1 measures a chlorine concentration in the sample water as the characteristic of the sample water. That is, in one or more embodiments, it is supposed that a measurement target is chlorine. The measurement target is not limited to chlorine and may be various other substances.

The measuring unit includes a control unit 10 (controller), a power source 20, an ammeter 26, a first electrode 21, and a second electrode 22.

A control unit 10 measures a current flowing in the sample water by controlling a power source 20 and an ammeter 26 and calculates a chlorine concentration in the sample water based on the measurement result of the current. The control unit 10 may be configured by including a processor such as a CPU (central processing unit). The control unit 10 may realize a predetermined function by causing the processor to execute a predetermined program.

The measuring device 1 may be further provided with a storage unit. The storage unit may store various information used in an operation of the control unit 10, programs for realizing functions of the control unit 10, or the like. The storage unit may function as a work memory of the control unit 10. The storage unit may be constituted by, for example, a semiconductor memory. The storage unit may be included in the control unit 10 or be configured separately from the control unit 10.

The measuring device 1 may be further provided with an output unit. The output unit outputs information acquired from the control unit 10. Specifically, the output unit outputs the chlorine concentration in the sample water calculated by the control unit 10. The output unit may notify information to a user by outputting visual information such as characters, shapes, or images, directly or via an external device or the like. The output unit may be provided with a display device or have a wired or wireless connection to a display device. The display device may include various displays, such as a liquid-crystal display. The output unit may notify information to the user by outputting aural information such as audio directly or via an external device or the like. The output unit may be provided with an audio output device such as a speaker or have a wired or wireless connection to an audio output device. The output unit may notify information to the user by outputting not only visual information or aural information but also information that the user can sense by another sense, directly or via an external device or the like. The output unit may be included in the control unit 10 or be configured separately from the control unit 10.

The first electrode 21 and the second electrode 22 are housed in the measuring tank 40 so as to be immersed in the sample water stored in the measuring tank 40. The power source 20 is connected in series between the first electrode 21 and the second electrode 22 and produces a potential difference between the first electrode 21 and the second electrode 22. By the power source 20 producing a potential difference between the first electrode 21 and the second electrode 22, a current flows through sample water positioned between the first electrode 21 and the second electrode 22.

The first electrode 21 has a main body and a working electrode 23. The main body is configured as a cylinder and is inserted in the measuring tank 40. The main body is constituted by an insulator such as a resin. The working electrode 23 is positioned on a tip side (side inserted in the measuring tank 40) of the main body so as to be immersed in the sample water, and it flows a current through the sample water by contacting the sample water. The current flowing through the sample water flows to the first electrode 21 through the working electrode 23. The working electrode 23 is configured to include, for example, a metal such as gold (Au) or another conductive material. In one or more embodiments, it is supposed that the working electrode 23 is configured by including gold.

The ammeter 26 is connected in series to a circuit connecting the first electrode 21, the second electrode 22, and the sample water and measures the magnitude of the current flowing through the sample water. The ammeter 26 may be configured to include an amplifier circuit.

The magnitude of the current flowing through the sample water is determined based on at least the chlorine concentration in the sample water. Accordingly, the control unit 10 can acquire the measurement result of the current from the ammeter 26 and calculate the chlorine concentration in the sample water based on the measurement result. The control unit 10 may calculate the chlorine concentration in the sample water based also on a magnitude of the potential difference produced between the first electrode 21 and the second electrode 22. The control unit 10 may calculate the chlorine concentration in the sample water based also on a shape of a portion immersed in the sample water of the first electrode 21 and the second electrode 22. The control unit 10 may generate a function or table of a calibration curve based on a measurement result of a current flowing through standard sample water having a known chlorine concentration. The control unit 10 may calculate the chlorine concentration in the sample water based on a measurement result of the current flowing through the sample water and a calibration curve.

The current flowing through the sample water is limited by a magnitude of a diffusion current that flows via the sample water between the working electrode 23 and the second electrode 22. That is, the ammeter 26 measures the magnitude of the diffusion current flowing between the working electrode 23 and the second electrode 22.

The magnitude of the diffusion current is greatly affected by a state of a diffusion layer produced near a surface of the working electrode 23. Accordingly, the more stable the state of the diffusion layer, the more stable the measured value of the magnitude of the diffusion current by the ammeter 26. The diffusion layer is formed by a concentration distribution of ions of the sample water near the surface of the working electrode 23. The concentration distribution of ions of the sample water near the surface of the working electrode 23 is produced by a current flowing through the sample water. The state of the diffusion layer is stabilized by stabilizing a concentration distribution of ions of the sample water near the surface of the working electrode 23.

The ion concentration distribution of the sample water near the surface of the working electrode 23 changes according to the diffusion current. By sample water positioned near the surface of the working electrode 23 being stably interchanged, the ion concentration distribution of the sample water near the surface of the working electrode 23 stabilizes to a steady state. The measuring device 1 stably interchanges the sample water near the surface of the working electrode 23 by rotating the first electrode 21 having the working electrode 23.

Therefore, the measuring unit is further provided with a motor 30 that rotates the first electrode 21. The first electrode 21 may be formed in a rod shape having a longitudinal direction. The motor 30 is connected to the first electrode 21 such that the first electrode 21 rotates around a rotational axis 21A along the longitudinal direction of the first electrode 21. The motor 30 can rotate at a variable rotational velocity in the period when the measuring device 1 is in a started state. For example, the rotational velocity of the motor 30 can be raised and lowered. That is, the motor 30 is configured to be able to change its rotational velocity. The motor 30 can stop rotation by making the rotational velocity zero while the measuring device 1 is still in the started state. In one or more embodiments, the rotational velocity may be equivalent to a rotational speed, a rotational frequency or the like in the controlling of the motor.

The rotational velocity of the motor 30 affects the ion concentration distribution of the sample water near the surface of the working electrode 23. As a result, the rotational velocity of the motor 30 affects the magnitude of the diffusion current. Specifically, the higher the rotational velocity of the motor 30, the greater the diffusion current that flows through the sample water having the same chlorine concentration. By raising the rotational velocity of the motor 30, the measuring device 1 can increase the diffusion current and facilitate calculating the chlorine concentration, even when the chlorine concentration of the sample water is low. That is, the measuring device 1 can raise a detection sensitivity of the chlorine concentration by raising the rotational velocity of the motor 30.

Furthermore, the motor 30 can change the direction of rotation. Specifically, the motor 30 can rotate the first electrode 21 clockwise or counterclockwise when viewing the first electrode 21, along the longitudinal direction thereof, from the motor 30 and in a direction of the measuring tank 40. In one or more embodiments, clockwise and counterclockwise rotation of the first electrode 21 are respectively referred to as rotation in a forward direction and rotation in a reverse direction. A rotational velocity of when the first electrode 21 rotates in the forward direction is represented by a positive value. A rotational velocity of when the first electrode 21 rotates in the reverse direction is represented by a negative value.

As above, the rotational velocity of the motor 30 affects the magnitude of the diffusion current. However, the rotational direction of the motor 30 does not affect the magnitude of the diffusion current. When the rotational velocity of the motor 30 may become a negative value, the greater the absolute value of the rotational velocity of the motor 30, the greater the diffusion current.

The measuring unit further includes the slip ring 25 and the brush 24 so as to be electrically connected to the power source 20 even in a state wherein the first electrode 21 is rotating. The slip ring 25 rotates together with the first electrode 21 by being driven by the motor 30. The brush 24 is disposed so as to contact a cylindrical surface of the slip ring 25. The brush 24 is biased toward the slip ring 25 so as to continue to contact the slip ring 25 even while the slip ring 25 is rotating.

The measuring tank 40 includes a first electrode housing portion 41 that houses the first electrode 21 and a second electrode housing portion 42 that houses the second electrode 22. The measuring tank 40 stores the sample water in the first electrode housing portion 41 and the second electrode housing portion 42. The measuring tank 40 is further provided with a passage 43 wherethrough the sample water passes between the first electrode housing portion 41 and the second electrode housing portion 42. The measuring tank 40 is further provided with an inlet that accepts the sample water and an outlet that discharges the sample water.

As above, a diffusion current flows between the surface of the working electrode 23 and the sample water. Here, the magnitude of the diffusion current is determined based on a surface area of the working electrode 23. When dirt is adhered to the surface of the working electrode 23, an effective surface area whereby the diffusion current flows to the working electrode 23 decreases. That is, dirt on the surface of the working electrode 23 affects the magnitude of the diffusion current.

Therefore, so dirt on the surface of the working electrode 23 can be cleaned, the measuring device 1 rotates the first electrode 21 while causing the surface of the working electrode 23 to contact granular members 44 such as ceramic beads or glass beads. To cause the surface of the working electrode 23 to contact the granular members 44, the measuring tank 40 houses the granular members 44 together with the sample water in the first electrode housing portion 41. That is, the granular members 44 are positioned inside the measuring tank 40. By doing so, when the first electrode 21 is housed in the first electrode housing portion 41, the granular members 44 contact the working electrode 23. By rotating the first electrode 21 in a state wherein the granular members 44 are contacting the working electrode 23, the granular members 44 produce friction against the surface of the working electrode 23 and reduce dirt adhered to the surface of the working electrode 23. That is, the granular members 44 can clean the surface of the working electrode 23.

The surface of the working electrode 23 is cleaned by the granular members 44 but is also deformed and abraded due to the friction with the granular members 44. Deformation or abrasion of the surface of the working electrode 23 causes the diffusion current flowing via the sample water between the working electrode 23 and the second electrode 22 to become unstable.

For example, when the working electrode 23 is constituted by a metal, the working electrode 23 is stretched thin over a surface of the main body of the first electrode 21 due to the friction with the granular members 44. By the working electrode 23 being stretched, the surface area of the working electrode 23 changes. Moreover, by the working electrode 23 being abraded, the surface area of the working electrode 23 can become small. A change in the surface area of the working electrode 23 changes the magnitude of the diffusion current and causes the diffusion current to become unstable. As a result, a calculation precision of the chlorine concentration in the sample water decreases.

Furthermore, by the working electrode 23 being stretched, the working electrode 23 becomes thin and more likely to be peeled from the first electrode 21. When the working electrode 23 is about to be or is actually peeled from the first electrode 21, the diffusion current can suddenly change. That is, separation of the working electrode 23 causes the diffusion current to become unstable. As a result, a calculation precision of the chlorine concentration in the sample water decreases.

In light of the above, deformation or abrasion of the working electrode 23 causes the diffusion current to become unstable. Therefore, when the working electrode 23 is deformed or abraded, the first electrode 21 must be replaced. As a result, deformation or abrasion of the surface of the first electrode 21 shortens the life of the electrode.

(Operational Example of Measuring Device 1)

The measuring device 1 according to one or more embodiments can prolong the life of parts by, for example, being operated as follows.

<Switching Between Measuring Mode and Standby Mode>

The control unit 10 continues to flow the diffusion current through the sample water when the measuring device 1 is in the started state. Meanwhile, the control unit 10 measures the diffusion current by a predetermined sampling period and calculates the chlorine concentration in the sample water. Said conversely, the control unit 10 does not measure the diffusion current other than at a timing determined by the predetermined sampling period. That is, the control unit 10 can switch an operation mode of the measuring device 1 between a measuring mode of measuring the diffusion current flowing through the sample water and a standby mode of not measuring the diffusion current.

As above, the rotational velocity of the motor 30 affects the magnitude of the diffusion current. Therefore, when operating in the measuring mode, the control unit 10 controls the rotational velocity of the motor 30 to a predetermined value for measurement. Meanwhile, when operating in the standby mode, the control unit 10 does not need to control the rotational velocity of the motor 30 to a predetermined value.

Here, the higher the rotational velocity of the motor 30, the easier it is for deformation or abrasion of the working electrode 23 of the first electrode 21 to advance. Moreover, the easier it is for abrasion of the slip ring 25 to advance.

<<Stoppage or Speed Reduction of Motor 30>>

The control unit 10 of the measuring device 1 according to one or more embodiments may set the rotational velocity of the motor 30 to zero to stop rotation of the first electrode 21 when operating in the standby mode. Thus, the deformation or abrasion of the working electrode 23 or the abrasion of the slip ring 25 less readily progresses. As a result, the life of each part is prolonged. Furthermore, when the first electrode 21 is continuously rotated while the supply of the sample water is stopped, the frictional force acting between the first electrode 21 and the granular members 44 becomes larger than when underwater. As a result, the first electrode 21 is depleted quickly, and the first electrode 21 may fail depending on the case. The measuring device 1 may reduce the risk of the depletion or failure of the first electrode 21 by automatically stopping the rotation of the motor 30 when detecting a decrease of the sample water in the measuring tank 40. Additionally, by automatically starting the rotation of the motor 30 when the supply of the sample water returns to normal, the measuring device 1 can realize intermittent measurement that saves the sample water. The measuring device 1 can detect whether the sample water is reduced or whether the sample water is present by varying the voltage between the two electrodes and detecting the change in the current flowing between the two electrodes. The measuring device 1 measures the resistance value between the two electrodes based on the change in current and may determine whether the sample water is reduced or whether the sample water is present based on the measurement result of the magnitude of the resistance value.

When the rotation of the first electrode 21 stops, the ion concentration distribution of the sample water near the surface of the working electrode 23, that is, the state of the diffusion layer may deviate greatly from the steady state. In this case, the amount of time required from restarting of the rotation of the first electrode 21 until the state of the diffusion layer near the surface of the working electrode 23 returns to the steady state can be prolonged because the measuring device 1 operates in the measuring mode. As a result, the amount of time required for the measuring device 1 to return from operation in the standby mode to operation in the measuring mode and to return to the state in which the measurement can be restarted becomes prolonged.

By not making the absolute value of the rotational velocity of the motor 30 zero, the degree to which the state of the diffusion layer deviates from the steady state is reduced compared to when stopping the motor 30. Thus, when the rotational velocity of the motor 30 is returned to the rotational velocity when operating in the measuring mode, the amount of time required until the state of the diffusion layer near the surface of the working electrode 23 returns to the steady state is shortened. Therefore, when operating in the standby mode, the measuring device 1 can shorten the amount of time to return to the operation in the measuring mode and extend the life of parts by making the absolute value of the rotational velocity of the motor 30 smaller than the absolute value of the rotational velocity when operating in the measuring mode without setting it to zero.

<<<Changing the Direction of Rotation of the Motor 30>>>

When the direction of rotation of the motor 30 is in a fixed direction, the surface of the working electrode 23 is stretched in the fixed direction by continuously receiving frictional force in the fixed direction from the granular members 44. The measuring device 1 according to one or more embodiments may alternatingly change the direction of rotation of the motor 30 between a forward direction and a reverse direction. By alternatingly changing the direction of rotation of the motor 30, the direction of the frictional force received by the surface of the working electrode 23 is changed alternatingly. Thus, the surface of the working electrode 23 is not stretched only in one direction. Furthermore, the surface of the working electrode 23 can be pulled back in the opposite direction even when extended in one direction. Thus, the surface area of the working electrode 23 less readily changes. As a result, the magnitude of the diffusion current is stabilized. Furthermore, the working electrode 23 is less readily peeled off. As a result, the life of the first electrode 21 is prolonged.

<Cleaning Mode>

The measuring device 1 may be dirtied by the sample water. Dirt adhered to the first electrode 21 and the second electrode 22 affects the detection accuracy of chlorine concentration. Furthermore, although the first electrode 21 is less readily dirtied by contact with the granular members 44, it is dirtied to a certain extent. Accordingly, the manager of the measuring device 1 must properly clean the first electrode 21 and the like. The measuring device 1 according to one or more embodiments may operate in a cleaning mode for cleaning the first electrode 21 and the like. When operating in the cleaning mode, the control unit 10 drives the motor 30 while the first electrode 21 and the second electrode 22 are pulled up out of the measuring tank 40 to rotate the first electrode 21. By cleaning equipment such as a brush or a cloth being pressed against the first electrode 21 in a state wherein the first electrode 21 is rotating, the labor of cleaning the first electrode 21 can be reduced.

The control unit 10 may control the motor 30 such that the rotational velocity of the motor 30 when operating in the cleaning mode is different from the rotational velocity when operating in the measuring mode. Thus, the rotation of the motor 30 can be controlled at a rotational velocity suitable for cleaning. As a result, dirt on the surface of the first electrode 21 can be efficiently removed.

Furthermore, when operating in the cleaning mode, the control unit 10 may alternatingly switch the rotating direction of the motor 30 between the forward direction and the reverse direction. Thus, by simply pressing the cleaning tool against the first electrode 21, dirt adhered to the first electrode 21 can be easily scraped off by a reciprocating motion. As a result, dirt on the surface of the first electrode 21 can be efficiently removed. Concerning the direction of rotation of the motor 30, when operating in at least one of the measuring mode and the cleaning mode, the control unit 10 may control the rotation of the motor 30 so as to alternatingly change the rotational velocity of the motor 30 between a positive value and a negative value.

<Breaking in Mode>

In the measuring device 1, the granular members 44 such as ceramic beads or glass beads in contact with the surface of a first electrode 21 are abraded by friction with the first electrode 21. That is, the granular members 44 are suitably replaced as a consumable.

In this case, the newly exchanged granular members 44 have very fine surface projections like konpeitō, to give an extreme example. The projections on the surface of the granular members 44 decrease as the first electrode 21 rotates and the friction with the granular members 44 continues. As a result, the surface of the granular members 44 becomes smooth.

The surface state of the granular members 44, the frictional state between the first electrode 21 and the granular members 44, or the frictional state of the granular members 44 between each other is relatively greatly changed in the initial stage of operation after replacement and tends to stabilize once in operation for a certain extent. The more these states stabilize, the more the magnitude of the diffusion current and the calculation result of the chlorine concentration in the sample water stabilize. Conversely, the calculation result of the chlorine concentration in the sample water may drift until the surface state or the frictional state of the granular members 44 has stabilized.

Therefore, the measuring device 1 according to one or more embodiments operates in a breaking in mode immediately after the replacement of the granular members 44. When operating in the breaking in mode, the control unit 10 sets the rotational velocity of the motor 30 higher than the rotational velocity when operating in the measuring mode. The surface state or frictional state of the granular members 44 stabilizes as the number of rotations of the first electrode 21 increases. Accordingly, the amount of time until the state stabilizes is shortened by increasing the rotational velocity of the motor 30.

<Setting Rotational Velocity According to Environment>

The measuring device 1 may, for example, be operated in an environment in which dirt does not readily adhere to the first electrode 21, such as an environment in which the dirtying components capable of adhering to the first electrode 21 are not abundant in the sample water. In such an environment, the measuring device 1 can set the rotational velocity of the motor 30 without considering removal of dirt adhering to the first electrode 21. Thus, the measuring device 1 can reduce the rotational velocity of the motor 30. By reducing the rotational velocity of the motor 30 to reduce the rotational velocity of the first electrode 21, the deformation or abrasion of the first electrode 21 or the abrasion of the slip ring 25 less readily progresses. As a result, the life of each part is extended.

<Sensitivity Adjustment>

The magnitude of the diffusion current flowing in the working electrode 23 may vary according to individual differences in the working electrode 23 even when the sample water has the same chlorine concentration. The diffusion current differing according to the individual differences in the working electrode 23 may cause differences in sensitivity. Therefore, the measuring device 1 may correct the sensitivity for each device by calibration. The calibration work may be performed whenever replaced with a different working electrode 23. Assuming that the calibration work is performed by an erroneous operation, the measured value of the measuring device 1 may become abnormal or may have a large error.

As described above, the higher the rotational velocity of the motor 30, the higher the detection sensitivity of the chlorine concentration. The control unit 10 compensates the magnitude of the diffusion current by changing the rotational velocity of the motor 30 and reduces the individual difference in the sensitivity of the measuring device 1 to make the sensitivity constant or stabilize it. Specifically, the control unit 10 calculates the chlorine concentration by measuring the current of the standard sample water having a known chlorine concentration and sets the rotational velocity of the motor 30 such that the calculation result matches the known chlorine concentration. The measuring device 1 stores the difference in this setting of the rotational velocity using one representative device at the time of production and assigns a value to such as a value unique to the first electrode 21. The measuring device 1 may store a set value by installing an ID chip on an electrode. The first electrode 21 assigned a value can be measured at the same sensitivity insofar as it operates at the set rotational velocity even when attached to another residual chlorine meter. By reducing the sensitivity difference when exchanging electrodes and simplifying calibration work, error due to incorrect calibration may be reduced.

As described above, the measuring device 1 according to one or more embodiments can realize various operation modes by making the rotational velocity of the motor 30 rotating the first electrode 21 variable. Thus, extension of the life of parts, setting of the detection sensitivity of chlorine concentration, reduction of the error of calculation results of chlorine concentration, and the like are realized. As a result, the convenience of the measuring device 1 is improved.

The measuring device 1 according to one or more embodiments described above measures a chlorine concentration in the sample water as a characteristic of the sample water. The measuring device 1 may be configured so as to distinguish between the free chlorine concentration and the bound chlorine concentration for the chlorine concentration in the sample water. Furthermore, the measuring device 1 is not limited to the concentration of chlorine in the sample water as the characteristics of the sample water and may, for example, be configured so as to measure the concentration of a metal ion in the sample water. That is, the measuring device 1 may be configured as a metal ion concentration meter. When the measuring device 1 is configured as a metal ion concentration meter, the granular members 44 may or may not be used. Furthermore, the measuring device 1 may also be configured as a bromine meter for measuring a bromine concentration in the sample water. Moreover, the measuring device 1 may also be configured as an iodine meter for measuring an iodine concentration in the sample water.

The first electrode 21 may be formed in a disc shape having a central axis. In this case, the motor 30 is connected to the first electrode 21 such that the first electrode 21 rotates around the central axis.

A measuring unit of the measuring device 1 according to one or more embodiments has been described as having a first electrode 21 and a second electrode 22. The measuring unit may further have a third electrode. The third electrode determines a potential as a reference when applying a voltage to the first electrode 21 and the second electrode 22. The third electrode does not contribute to the current flowing in the sample water. Due to the measuring unit having a third electrode, the second electrode 22 leaches less readily.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

1: Measuring device, 10: control unit, 20: power source, 21: first electrode, 21A: rotational axis, 22: second electrode, 23: working electrode, 24: brush, 25: slip ring, 26: ammeter, 30: motor, 40: measuring tank, 41: first electrode housing portion, 42: second electrode housing portion, 43: passage, 44: granular members

What is claimed is:

1. A measuring device, comprising:
a first electrode and a second electrode immersed in sample water stored in a measuring tank;
a motor that rotates the first electrode; and
a controller that operates, based on measurement results of current flowing through the sample water, in a measuring mode, wherein
in the measuring mode, the controller calculates a concentration of a measurement target in the sample water,
the motor changes a rotational velocity of the first electrode,
the controller operates in a standby mode wherein the concentration of the measurement target in the sample water is not calculated, and
when the controller operates in the standby mode, the controller controls the motor such that a first absolute value of the rotational velocity when operating in the standby mode is larger than zero and smaller than a second absolute value of the rotational velocity when operating in the measuring mode.

2. The measuring device according to claim 1, wherein the first electrode:
rotates either clockwise or counterclockwise as a forward direction when the rotational velocity is a positive value; and
rotates in a direction opposite to the forward direction when the rotational velocity is a negative value, and
the controller controls the motor such that the rotational velocity is alternately changed between the positive value and the negative value.

3. The measuring device according to claim 2, wherein the controller operates in a cleaning mode wherein the first electrode is cleaned, and
when the controller operates in at least one mode of the measuring mode or the cleaning mode, the controller controls the motor such that the rotational velocity is alternatingly changed between the positive value and the negative value.

4. The measuring device according to claim 3, further comprising:
granular members disposed inside the measuring tank and that contact a surface of the first electrode, wherein
the controller operates in a breaking mode after the granular members are replaced, and
the controller controls the motor such that a third absolute value of the rotational velocity when operating in the breaking mode is larger than the second absolute value.

5. The measuring device according to claim 3, wherein the controller controls the rotational velocity based on a magnitude of a current flowing in a standard sample water having a known measurement target concentration.

6. The measuring device according to claim 2, further comprising:
granular members disposed inside the measuring tank and that contact a surface of the first electrode, wherein
the controller operates in a breaking mode after the granular members are replaced, and
the controller controls the motor such that a third absolute value of the rotational velocity when operating in the breaking mode is larger than the second absolute value.

7. The measuring device according to claim 2, wherein the controller controls the rotational velocity based on a magnitude of a current flowing in a standard sample water having a known measurement target concentration.

8. The measuring device according to claim 1, further comprising:
granular members disposed inside the measuring tank and that contact a surface of the first electrode, wherein
the controller operates in a breaking mode after the granular members are replaced, and
the controller controls of the motor such that a third absolute value of the rotational velocity when operating in the breaking mode is larger than the second absolute value.

9. The measuring device according to claim 8, wherein the controller controls the rotational velocity based on a magnitude of a current flowing in a standard sample water having a known measurement target concentration.

10. The measuring device according to claim 1, wherein the controller controls the rotational velocity based on a magnitude of a current flowing in a standard sample water having a known measurement target concentration.

* * * * *

UNITED STATES PATENT AND TRADEMARK OFFICE
CERTIFICATE OF CORRECTION

| | |
|---|---|
| PATENT NO. | : 11,946,899 B2 |
| APPLICATION NO. | : 17/463772 |
| DATED | : April 2, 2024 |
| INVENTOR(S) | : Kyakuno et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this
Fifteenth Day of October, 2024

Katherine Kelly Vidal
*Director of the United States Patent and Trademark Office*